(12) United States Patent
Liu et al.

(10) Patent No.: US 10,079,387 B2
(45) Date of Patent: Sep. 18, 2018

(54) ELECTRICAL CONDUCTIVE POLYMER BINDER FOR SI ALLOY MATERIALS

(71) Applicants: Gao Liu, Piedmont, CA (US); Hui Zhao, Emeryville, CA (US)

(72) Inventors: Gao Liu, Piedmont, CA (US); Hui Zhao, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 73 days.

(21) Appl. No.: 14/632,907

(22) Filed: Feb. 26, 2015

(65) Prior Publication Data

US 2015/0243996 A1 Aug. 27, 2015

Related U.S. Application Data

(60) Provisional application No. 61/944,976, filed on Feb. 26, 2014.

(51) Int. Cl.
| | |
|---|---|
| *C07C 235/74* | (2006.01) |
| *H01M 4/62* | (2006.01) |
| *H01M 4/04* | (2006.01) |
| *H01M 4/134* | (2010.01) |
| *H01M 4/1395* | (2010.01) |
| *H01M 4/38* | (2006.01) |
| *H01M 4/66* | (2006.01) |
| *C07C 235/78* | (2006.01) |
| *H01M 4/02* | (2006.01) |
| *H01M 10/0525* | (2010.01) |

(52) U.S. Cl.
CPC .......... *H01M 4/622* (2013.01); *C07C 235/78* (2013.01); *H01M 4/0404* (2013.01); *H01M 4/134* (2013.01); *H01M 4/1395* (2013.01); *H01M 4/386* (2013.01); *H01M 4/387* (2013.01); *H01M 4/661* (2013.01); *C07C 235/74* (2013.01); *H01M 10/0525* (2013.01); *H01M 2004/027* (2013.01); *Y02E 60/122* (2013.01)

(58) Field of Classification Search
CPC .... H01M 4/622; H01M 4/0404; H01M 4/134; H01M 4/1395; H01M 4/386; H01M 4/661; H01M 2004/027; H01M 10/0525; H01M 4/387; Y02E 60/122; C07C 235/78; C07C 235/74
USPC ............... 429/217; 252/512, 513; 427/126.1; 560/39
See application file for complete search history.

(56) References Cited

U.S. PATENT DOCUMENTS

| | | | |
|---|---|---|---|
| 2006/0105240 A1* | 5/2006 | Kinoshita | H01M 4/131 429/231.3 |
| 2012/0078296 A1* | 3/2012 | Lee | C08G 65/33389 606/214 |
| 2013/0122368 A1* | 5/2013 | Shinya | H01M 4/386 429/218.1 |

OTHER PUBLICATIONS

"A versatile macro-initiator with dual functional anchoring groups for surface-initiated atom transfer radical polymerization on various substrates", by Qiangbing Wei, et al. In Polymer Chemistry, Year 2012, vol. 3, pp. 2129-2137.*

* cited by examiner

*Primary Examiner* — Jonathan G Jelsma
*Assistant Examiner* — Omar M Kekia
(74) *Attorney, Agent, or Firm* — Stuart B. Chinn; Lawrence Berkeley, National Laboratory

(57) ABSTRACT

A Poly(1-pyrenemethyl methacrylate-co-dopamine methacrylamide) PPyDMA polymer binder has been designed and fabricated, and has demonstrated an excellent performance for silicon (Si), graphite and a metal alloy anode materials. The PPyDMA polymer binder demonstrates the great potential of a catechol moiety for use in a lithium-ion battery.

14 Claims, 4 Drawing Sheets

ELECTRICAL CONDUCTIVE POLYMER BINDER FOR SI ALLOY MATERIALS

CROSS REFERENCE TO RELATED APPLICATIONS

This U.S. Utility application claims priority to U.S. Provisional Application Ser. No. 61/944,976 filed Feb. 26, 2014, which application is incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

Field of the Invention

The present invention relates to the field of Lithium ion batteries.

Related Art

State of the art Li-ion negative electrodes employ graphitic active materials with theoretical capacities of 372 mAh/g. Development of new high-capacity anode materials, such as Sn, Si and other alloy anodes, has been one of the major focuses of the research in lithium-ion battery field.

Silicon (Si) possesses a theoretical capacity of 4200 mAh/g, while Tin (Sn) has a theoretical capacity of 994 mAh/g for full lithiation to the $Li_{22}M_5$ phase wherein M is a metal, such as Si or Sn. However, despite their remarkable high capacity and the intensive research done in the field, there have been no widespread applications of Si or Sn alloy anodes in lithium-ion cells, mostly due to the large volume change associate with lithiation and delithiation of the material. This volume change disrupts the integrity of electrode and induces excessive side reactions, leading to fast capacity fade. Several polymer binders were successfully applied for the alloy anodes, such as carboxymethyl cellulose (CMC) and polyacrylic acid (PAA). It has been shown that a thin oxide layer with a thickness of several nanometers exist in the commercial Si particles. The interaction between silanol and the carboxylic acid groups (see FIG. 1b) on CMC or PAA plays a very important role to maintain the adhesion of binder on the active material, as well as to keep the mechanical and electronic integrity of the electrode. However, the Si-based cell performance from the current binders continues to be unsatisfactory in terms of long-term capacity retention and efficiency. There is a demand to develop polymer binders with new structural moiety which offers better binding strength, which helps to avoid detachment of the binder from active particles during volume shrinkage after delithiation.

Since Lee et al. identified the catecholic amino acid 3,4-dihydroxy-L-phenylalanine (DOPA) as the main protein component that offers strong interfacial adhesion in mussel, polymer adhesives containing a catechol moiety (see FIG. 1a) have attracted major attention in this field. Since it is well-established that an oxide layer exists on the surface of the commercial metal alloy anodes, it is proposed that a polymer binder (see FIG. 1c) with a catechol side chain could interact with this surface oxide layer, generate a strong adhesion strength and maintain the electrode integrity during drastic volume change in lithiation and delithiation.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Various embodiments of the invention describe novel polymer binders such as Poly(1-pyrenemethyl methacrylate-co-dopamine methacrylamide) PPyDMA wherein 1-pyrenemethyl methacrylate refers to the PPy part and dopamine methacrylamide refers to the DMA (catechol).

Figure 1:
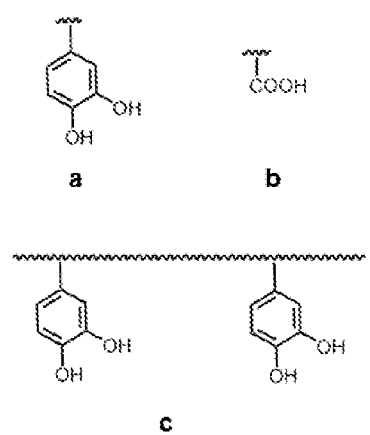
FIG. 1 illustrates chemical structures of (a) catechol, (b) carboxylic acid and (c) proposed polymer binder with catechol side chain for lithium-ion batteries.
Figure 2:
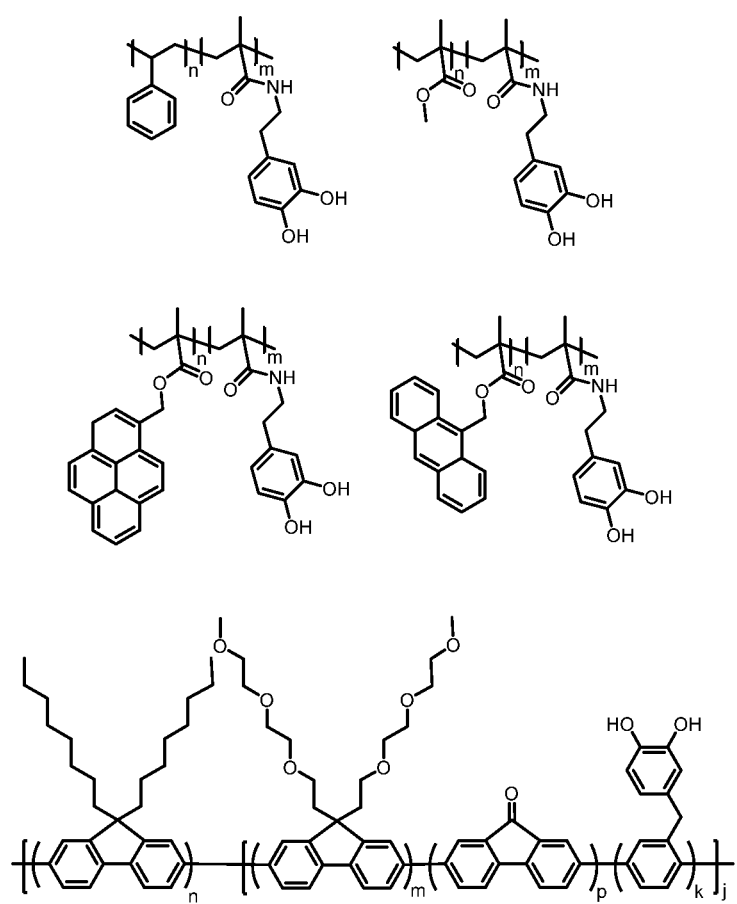
FIG. 2 illustrates polymer binder structures that contain catechol moiety for lithium-ion batteries.

FIG. 2 illustrates a series of representative polymer structures that contain a catechol moiety. These catechol containing polymers have been demonstrated to be excellent binders for use in Lithium-ion batteries. Conventional polymers such as poly(methyl methacrylate) and polystyrene have been facilely co-polymerized with N-(3,4-dihydroxyphenethyl) methacrylamide (DOMA) to form a catechol-containing polymer. Embodiments shown FIG. 2 demonstrate that pyrene and anthracene methacrylate catechol-containing polymers can enable Si-based, Sn-based, or Sn in inactive matrix (Al and Fe) lithium-ion batteries to perform with excellent cycling property, and that incorporation of the catechol-containing moiety enhances the binding property, which is of paramount importance to maintaining the mechanical and electronic integrity of high-capacity alloy-based anodes, such as Sn and Si anodes. As another example, the catechol moiety has also been incorporated into a polyfluorene-type polymer which has been shown to be a conductive polymer binder for alloy anodes.

To exemplify the use of dopamine-containing polymers as binders for lithium-ion batteries, in one embodiment we incorporated the catechol moiety into a pyrene-based methacrylate polymer. This random copolymer was obtained by free radical polymerization of N-(3,4-dihydroxyphenethyl) methacrylamide (DOMA) and pyrene methacrylate (PyMA), the final polymer contains 36.6 mol % of pDOMA.

Figure 3:
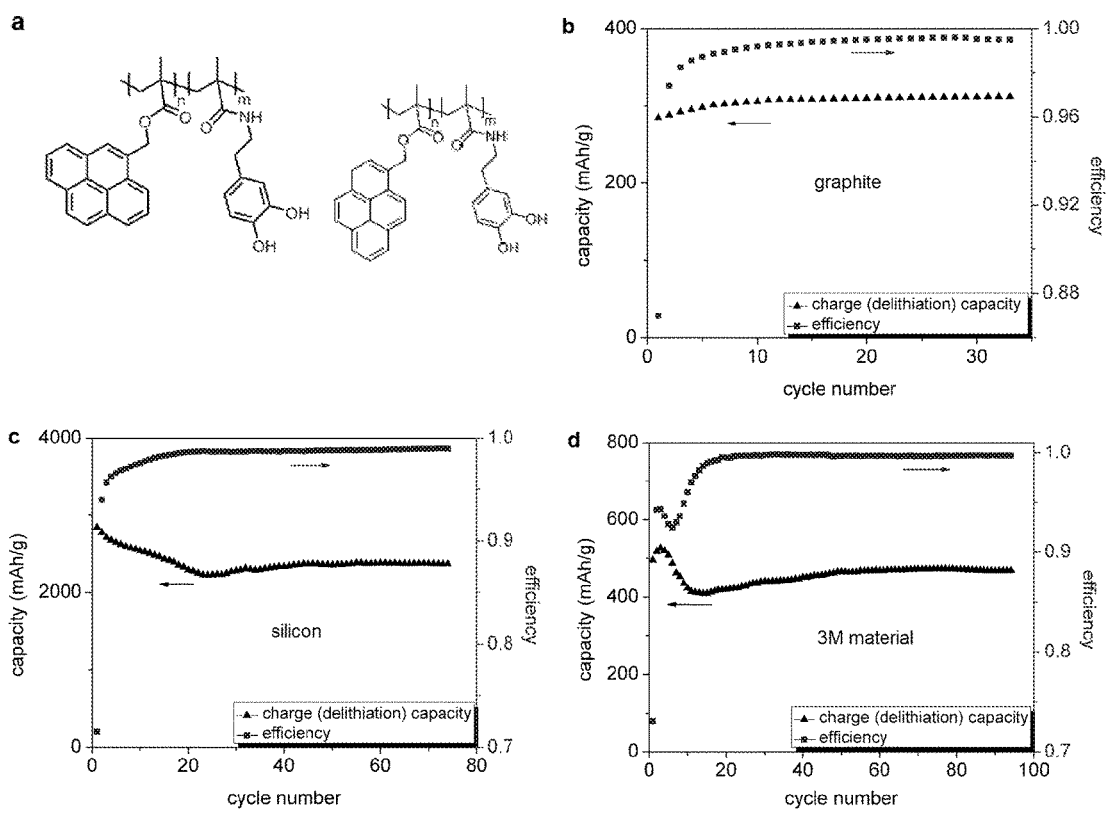
FIG. 3 illustrates (a) the chemical structure of p(DOMA)-(PyMA) binder, half cell cycling performance of (b) graphite at C/10 (31 mA/g) in EC/DEC=1, 1M $LiPF_6$, (c) silicon at C/10 (420 mA/g) in EC/DEC=3/7, 30% FEC, 1.2 M $LiPF_6$ and (d) Sn—Al—Fe alloy anode from 3M at C/10 (100 mA/g) in EC/EMC/DMC=1, 10% FEC, 1M $LiPF_6$.

FIG. 3 illustrates the chemical structure of the PPyDMA (alternatively pDOMA-PyMA) polymer binder we used, as well as its performance in graphite, silicon and a SN—Al—Fe alloy material commercialized by 3M. The laminates based on this polymer were fabricated by dispersing 90 wt % graphite, 66.7 wt % silicon or 90% 3M alloy active materials in the corresponding polymer/N-Methyl-2-pyrrolidone (NMP) solution. NMP is the solvent used to dissolve the polymer, make a slurry and fabricate the lithium ion electrode A Graphite-based (CGP-G8) half cell shows a reversible capacity of around 310 mAh/g in EC/DEC (the electrolytes contain ethylene carbonate (EC) and diethyl carbonate (DEC)), which is approximately similar in performance to a polyvinylidene (PVDF) binder. The Coulombic efficiency at $35^{th}$ cycle is about 99.50%. Anodes based on silicon nanoparticles reached a reversible capacity of around 2300 mAh/g after 100 cycles, the Coulombic efficiency at $80^{th}$ cycle is around 98.99%. A Sn—Al—Fe alloy anode, commercialized by 3M, utilizes an active material (Sn) in inactive matrix (Al and Fe). This micron-size material has an average particle size of 4~7 μm in diameter. A reversible capacity of ~460 mAh/g at C/10 was obtained with a Coulombic efficiency of 99.71% at $90^{th}$ cycle.

Figure 4:
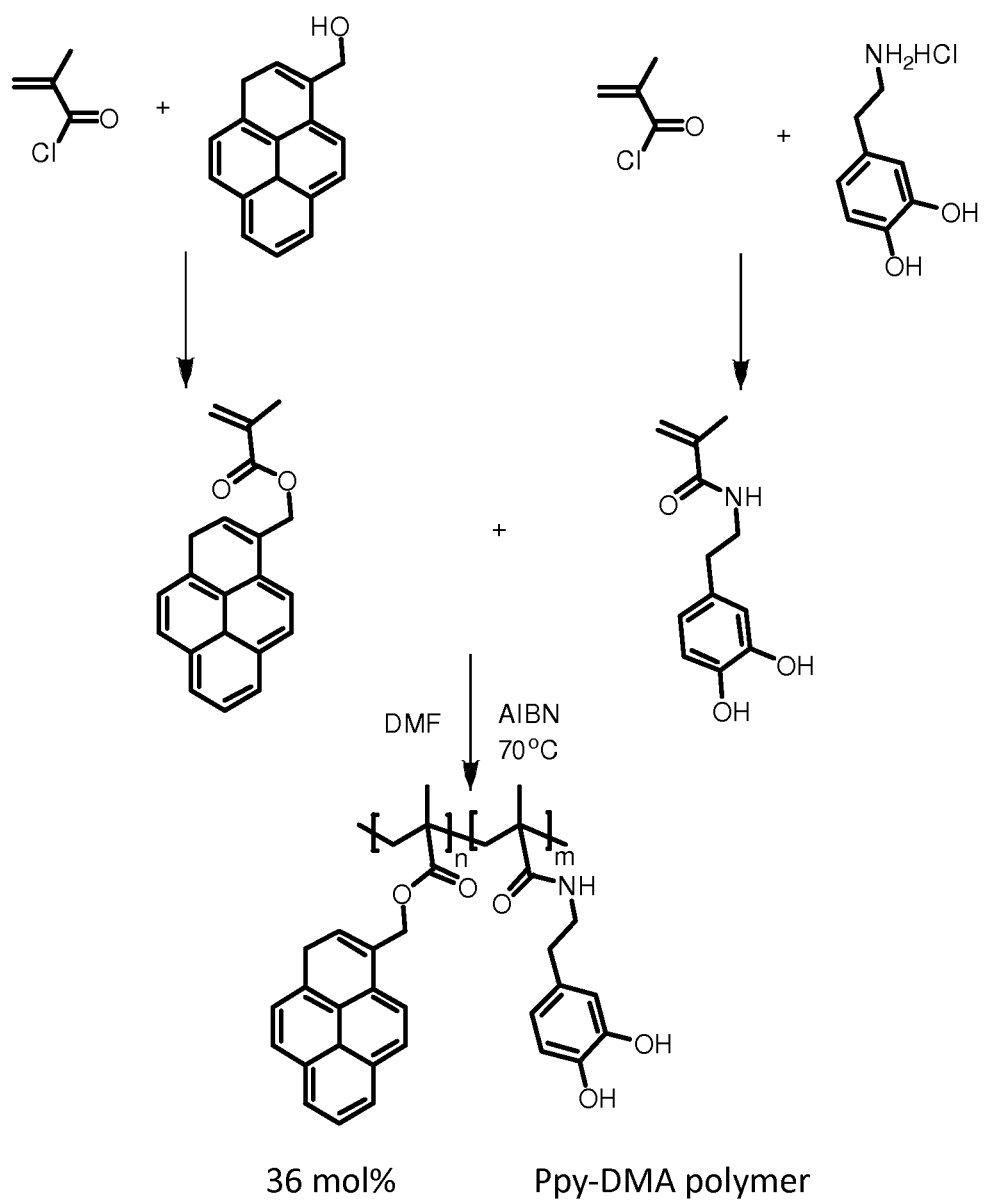
FIG. 4 illustrates a process to make Poly(1-pyrenemethyl methacrylate-co-dopamine methacrylamide) PPyDMA wherein 1-pyrenemethyl methacrylate refers to the PPy part and dopamine methacrylamide refers to the DMA (catechol).

FIG. 4 illustrates a process to make Poly(1-pyrenemethyl methacrylate-co-dopamine methacrylamide) PPyDMA wherein 1-pyrenemethyl methacrylate refers to the PPy part and dopamine methacrylamide refers to the DMA (catechol).

A Poly(1-pyrenemethyl methacrylate-co-dopamine methacrylamide) PPyDMA (alternatively pDOMA-PyMA) polymer binder has been designed and fabricated, and has demonstrated an excellent performance for Si, graphite and a metal alloy anode materials. The PPyDMA polymer binder demonstrates the great potential of a catechol moiety for use in a lithium-ion battery.

What is claimed is:

1. A polymeric composition with repeating units of the formula comprising:

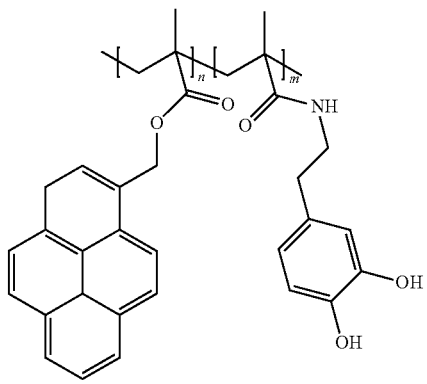

wherein n+m=1, and n>than 0 and m>than 0.

2. A composition of matter comprising:
an active electrode material selected from the group comprising silicon (Si), or tin (Sn), or Sn in inactive matrix (aluminum Al and iron Fe); and
a polymer binder, wherein the polymer binder comprises a polymeric composition having repeating units of the formula:

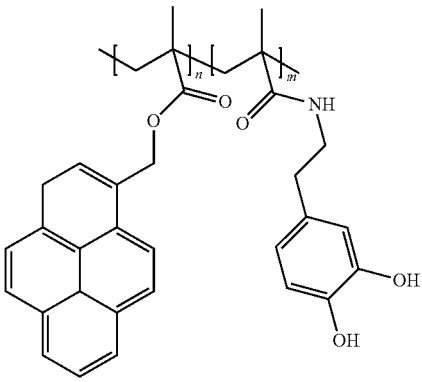

wherein n+m=1, and n>than 0 and m>than 0.

3. The composition of matter of claim 2 wherein the composition is deposited onto a copper foil.

4. The composition of matter of claim 3 wherein the composition is deposited onto the copper foil to form a film laminate.

5. The composition of matter of claim 4 wherein an exposed side of said film laminate includes a carbonate stabilizer.

6. The composition of matter of claim 5 wherein the carbonate stabilizer is ethylene carbonate or fluoroethylene carbonate.

7. The composition of matter of claim 5 wherein said carbonate stabilizer is an alkylene carbonate or alkyl carbonate.

8. The composition of matter of claim 5 wherein said carbonate stabilizer is a vinylene carbonate.

9. An electrode for use in a lithium-ion battery including the composition of matter of claim 2.

10. A lithium ion battery having a negative electrode, wherein said negative electrode comprises a laminate of the composition of matter of claim 2 in combination with a current collector.

11. The lithium ion battery of claim 10 wherein the laminate comprises a copper foil current collector in electrical contact with a covering layer of the composition of matter of claim 2.

12. A method of forming the laminate of claim 11 wherein Si, or Sn, or Sn in inactive matrix (Al and Fe) is combined with the polymer binder, the two components mixed in an organic solvent to form a slurry, the slurry then deposited onto the copper foil current collector followed by drying.

13. The method of claim 12 wherein, after formation, the exposed surface of the laminate is brought into contact with an alkylene carbonate or alkyl carbonate or ethylene carbonate or fluoroethylene carbonate to further stabilize the exposed surface.

14. The method of claim 13 wherein the carbonate is added to the electrolyte of the lithium ion battery to bring it into contact with the exposed surface of the laminate.

* * * * *